(12) United States Patent
Pilling et al.

(10) Patent No.: US 9,113,652 B2
(45) Date of Patent: Aug. 25, 2015

(54) USE OF ALTERNAN AS INGREDIENT FOR CERTAIN FOODSTUFFS

(75) Inventors: Jens Pilling, Dortmund (DE); Claus Frohberg, Kleinmachnow (DE)

(73) Assignee: BAYER INTELLECTUAL PROPERTY GMBH, Monheim am Rhein (DE)

( * ) Notice: Subject to any disclaimer, the term of this patent is extended or adjusted under 35 U.S.C. 154(b) by 299 days.

(21) Appl. No.: 12/735,570

(22) PCT Filed: Jan. 30, 2009

(86) PCT No.: PCT/EP2009/000762
§ 371 (c)(1),
(2), (4) Date: Jul. 28, 2010

(87) PCT Pub. No.: WO2009/095278
PCT Pub. Date: Aug. 6, 2009

(65) Prior Publication Data
US 2011/0189346 A1    Aug. 4, 2011

Related U.S. Application Data

(60) Provisional application No. 61/063,209, filed on Feb. 1, 2008, provisional application No. 61/068,908, filed on Mar. 11, 2008, provisional application No. 61/068,895, filed on Mar. 11, 2008.

(30) Foreign Application Priority Data

| Jan. 31, 2008 | (EP) | 08101169 |
| Mar. 7, 2008 | (EP) | 08102397 |
| Mar. 7, 2008 | (EP) | 08102399 |

(51) Int. Cl.

| A23G 3/00 | (2006.01) |
| A23L 1/30 | (2006.01) |
| A23L 1/054 | (2006.01) |
| A23L 1/09 | (2006.01) |
| A23L 1/308 | (2006.01) |
| A23L 2/52 | (2006.01) |
| C12P 19/04 | (2006.01) |
| C12P 19/18 | (2006.01) |

(52) U.S. Cl.
CPC .................. *A23L 1/30* (2013.01); *A23L 1/0546* (2013.01); *A23L 1/09* (2013.01); *A23L 1/308* (2013.01); *A23L 2/52* (2013.01); *C12P 19/04* (2013.01); *C12P 19/18* (2013.01)

(58) Field of Classification Search
CPC ........... A23L 1/09; A23L 1/308; C12P 19/04; C12P 19/18
USPC ................................................. 426/64, 658
See application file for complete search history.

(56) References Cited

U.S. PATENT DOCUMENTS

| 5,702,942 A | 12/1997 | Leathers et al. |
| 5,789,209 A | 8/1998 | Leathers et al. |
| 7,182,954 B1 | 2/2007 | Cote et al. |
| 2002/0106437 A1* | 8/2002 | Karleskind et al. ........... 426/590 |
| 2006/0141127 A1 | 6/2006 | Stephen et al. |
| 2007/0003670 A1 | 1/2007 | Jendrysik et al. |
| 2007/0172931 A1* | 7/2007 | Harrison et al. .............. 435/101 |
| 2007/0281059 A1* | 12/2007 | Smith .......................... 426/311 |
| 2008/0098975 A1 | 5/2008 | Morita et al. |

FOREIGN PATENT DOCUMENTS

| DE | 10209629 | 1/2004 |
| DE | 10209629 B3 * | 1/2004 |
| EP | 1738659 | 1/2007 |
| JP | 2005500839 | 1/2005 |
| JP | 2007006888 | 1/2007 |
| WO | WO 00/47727 | 8/2000 |
| WO | WO 03/008618 | 1/2003 |
| WO | WO 03/010177 | 2/2003 |
| WO | WO 2005/089483 | 9/2005 |
| WO | WO 2006/062410 | 6/2006 |
| WO | WO 2006/088884 | 8/2006 |
| WO | WO 2007/011222 | 1/2007 |
| WO | WO 2007/128559 | 11/2007 |

OTHER PUBLICATIONS

A Milosevic "Sports Drinks Hazard to Teeth" Published in British journal of Sports medicine 1997, 31:28-30 pp. 4.*
Maria Luz Sanz et al "Prebiotic Properties of Alternansucrose Maltose-Acceptor Oligosaccharides", Article in Journal of Agricultural and Food Chemistry 2005, 53 5911-5916, hereinafter Maria.*
Arguello-Morales et al., FEMS Microbiology Letters, vol. 182, pp. 81-85 (2000).
Cote et al., Carbohydrate Research, vol. 111, pp. 127-142 (1982).
Cote, Carbohydrate Polymers vol. 19, pp. 249-252 (1992).
Degenkolb et al, Antimicrobial Agents & Chemotherapy, vol. 35, No. 8, pp. 1591-1595 (1991).
Dotto et al, Proceedings National Academy Sciences, vol. 79, pp. 7122-7126 (1982).
Hardin, Agricultural Research, pp. 10-11 (1999).
Horn et al, Applied Microbiology and Biotechnology, vol. 46, pp. 524-532 (1996).
Jeong et al, Journal of Clinical Microbiology, vol. 42, No. 7, pp. 2902-2906 (2004).
Leathers et al, Carbohydrate Polymers vol. 54, pp. 107-113 (2003).
Lopez-Munguia et al, Enzyme Microbial Technology, vol. 15, pp. 77-85 (1993).
Schmidt et al., Protein Engineering, vol. 6, pp. 109-122 (1993).
Seymour et al., Carbohydrate Research, vol. 74, pp. 41-62 (1979).
Skerra, Gene, vol. 151, pp. 131-135 (1994).
International Search Report for International Patent Application No. PCT/EP2009/000762, mailed Aug. 3, 2009.

(Continued)

*Primary Examiner* — Jyoti Chawla
(74) *Attorney, Agent, or Firm* — Hunton & Williams LLP

(57) ABSTRACT

The invention is directed to the use of an alternan as an ingredient for acidic foodstuffs and to an acidic foodstuff comprising alternan as ingredient. The invention is also directed to the use of alternan as a heat stable ingredient in a foodstuff formulation, and to a foodstuff comprising alternan as ingredient, wherein the foodstuff was subjected to a heating step during its manufacture.

18 Claims, No Drawings

(56) References Cited

OTHER PUBLICATIONS

International Preliminary Report for Patentability for International Patent Application No. PCT/EP2009/000762, mailed Aug. 3, 2010.
Written Opinion for International Patent Application No. PCT/EP2009/000762, mailed Aug. 3, 2009.
High5 Sport Nutrition Products, http://highfive.co.uk/shop, retrieved Sep. 20, 2012.
High5 Sport Nutrition, http://highfive.co.uk/product/engergize/energy source, retrieved Sep. 20, 2012.
High5 Sport Nutrition, http://highfive.co.uk/product/engergize/energy source-plus, retrieved Sep. 20, 2012.
High5 Sport Nutrition, http://highfive.co.uk/product/engergize/energy source-Xtreme, retrieved Sep. 20, 2012.
High5 Sport Nutrition, http://highfive.co.uk/product/engergize/energy source-4:1, retrieved Sep. 20, 2012.
Email regarding: pH of Go energy drink from Carol Evans@scienceinsport.com to Andreas Beyer mailed Sep. 21, 2012.
SIS (Science in Sport) Limited GO Energy, http://www.scienceinsport.com/acatalog/GO_Energy.html, retrieved Sep. 24, 2012.
English Translation of Office Action mailed May 14, 2013 in JP App. No. 2010-544652.

\* cited by examiner

USE OF ALTERNAN AS INGREDIENT FOR CERTAIN FOODSTUFFS

CROSS-REFERENCE TO RELATED APPLICATIONS

This application is the U.S. National Stage filing of International Patent Application No. PCT/EP2009/000762, filed Jan. 30, 2009, which claims priority to EP 08101169.4, filed Jan. 31, 2008, U.S. Provisional Application No. 61/063,209, filed Feb. 1, 2008, EP 08102397.0, filed Mar. 7, 2008, EP 08102399.6, filed Mar. 7, 2008, U.S. Provisional Application No. 61/068,908, filed Mar. 11, 2008, and U.S. Provisional Application 61/068,895, filed Mar. 11, 2008. The disclosures of each of these applications are hereby incorporated by reference in their entirety.

FIELD OF INVENTION

The first invention is directed to the use of an alternan as ingredient for acidic foodstuffs and to an acidic foodstuff comprising alternan as ingredient.

BACKGROUND

Alternan poly- or oligosaccharides are composed of glucose units. The glucose units are linked to each other via α-1,3- and α-1,6-glycosidic bonds, and said two types of bonds predominantly appear alternatingly.

Alternan-oligosaccharides have been described as prebiotic ingredients. U.S. Pat. No. 7,182,954 discloses that oligosaccharides produced by an alternansucrase enzyme catalyzed reaction of sucrose with various acceptor sugars are effective as prebiotics for controlling enteric bacterial pathogens. Populations of enteropathogenic bacteria may be substantially reduced or inhibited by treatment of an animal with a composition comprising one or more of these oligosaccharides in an amount effective to promote the growth of beneficial bacteria (e.g. Lactobacilli, Bifidobacteria).

The publication WO2006088884 provides with methods of making substantially clear low-glycemic syrups (LGS) that comprise alternan oligosaccharides. These syrups have a relatively low glycemic index and are additionally useful in applications where increased clarity is desired. These qualities are particularly beneficial in foodstuff formulations.

However, the need persists for prebiotic food ingredients which retain their beneficial properties in low pH environments as it is the case in acidic foodstuffs, particularly acidic beverages.

DETAILED DESCRIPTION OF THE PREFERRED EMBODIMENTS OF THE INVENTION

Therefore, it is an object of the first invention to provide with a pH stable prebiotic and/or low glycemic and/or soluble fiber ingredient for foodstuffs.

A further object of the first invention is to provide with a pH and temperature-stable prebiotic and/or low glycemic and/or soluble fiber ingredient for acidic foodstuffs since foodstuffs are often processed at high temperatures.

The first invention is directed to the use of alternan as ingredient for acidic foodstuffs. Particularly, alternan is used as degradation-resistant ingredient for acidic foodstuffs.

Alternan is deemed to have prebiotic properties (Lopez-Munguia et al Enzyme Microb, Technol. 15 (1993)). Other beneficial properties have been described. According to U.S. Pat. No. 5,702,942 and U.S. Pat. No. 5,789,209 alternans have unique properties that resemble certain functional characteristics of gum arabic, maltodextrins or polydextrose (G. L. Cote, Carbohydrate Polymers 19:249-252 (1992)). Moreover, according to U.S. Pat. No. 5,702,942 and U.S. Pat. No. 5,789,209 alternan has potential commercial applications as a low-viscosity bulking agent and extender in foods and cosmetics, so that alternans have potential value as noncaloric, carbohydrate-based soluble food additives.

In the first invention it is shown that alternan is not degraded in acidic environment and could therefore retain the above-mentioned properties when added to an acidic foodstuff, particularly acidic beverages. In similar manner, the low glycemic properties and soluble fiber properties of alternan are retained in acidic foodstuffs, since no glucose is released from the alternan molecules.

The term "alternan" according to the first invention encompasses alternan-polysaccharide and alternan-oligosaccharide, wherein both types of alteran differ in their molecular weights, as further defined below.

Alternan according to the first invention is a saccharide composed of glucose units. The glucose units are linked to each other via α-1,3- and α-1,6-glycosidic bonds, and said two types of bonds predominantly appear alternatingly. Alternan may contain branches (Seymour et al., Carbohydrate Research 74, (1979), 41-62).

Alternan-polysaccharide according to the definition of the first invention has a weight average molecular weight Mw of more than 3 000 g/mol, preferably more than 5 000 g/mol (determined with GPC RI or GPC MALLS). In another embodiment, alternan-polysaccharide has a weight average molecular weight Mw in the range of 10 000 000 g/mol to 60 000 000 g/mol (determined with GPC MALLS), more preferably in the range of 12 000 000 g/mol to 50 000 000 g/mol. In a special embodiment, alternan-polysaccharide is produced with alternansucrase originating from *Leuconostoc Mesenteroides* as described in WO 00/47727 and shows a weight average molecular weight Mw in the range of 33 000 000 g/mol to 60 000 000 g/mol (determined with GPC MALLS), more preferably in the range of 33 000 000 g/mol to 50 000 000 g/mol. In still another special embodiment, alternan-polysaccharide is produced with truncated alternansucrase enzyme as described in PCT/EP2008/051760 and shows a weight average molecular weight Mw in the range of 12 000 000 g/mol to 30 000 000 g/mol (GPC MALLS), more preferably in the range of 14 000 000 g/mol to 28 000 000 g/mol, still more preferably in the range of 16 000 000 g/mol to 26 000 000 g/mol, most preferably 18 000 000 g/mol to 23 000 000 g/mol. Truncated alternansucrase enzymes, methods for producing alternan-polysaccharide therefrom as well as the alternan-polysaccharide itself are described in PCT/EP2008/051760, which is incorporated herein by reference in its entirety.

The weight average molecular weight Mw of alternan-oligosaccharide in the definition of the first invention is 3 000 g/mol or below, preferably 2 500 g/mol or below, more preferably 2 000 g/mol or below, still more preferably 1 500 g/mol or below and most preferably 1 300 g/mol or below (determined with GPC RI or GPC MALLS). Thus the weight average degree of polymerization DPw of alternan oligosaccharide according to the invention is 18.5 or below, preferably 15.4 or below, more preferably 12.3 or below, still more preferably 9.3 or below and most preferably 8.0 or below (DPw=Mw/162 g/mol, 162 g/mol=molecular weight of monomeric glucose unit). The lower limit of the weight average molecular weight Mw of alternan-oligosaccharide is in another embodiment 800 g/mol (DPw=4.9) and the Mw of alternan-oligosaccharide is in the range of 800 g/mol to 3 000 g/mol, preferably 800 g/mol to 2 500 g/mol, more preferably 800 g/mol to 2 000 g/mol, still more preferably 800 g/mol to 1 500 g/mol and most preferably 800 g/mol to 1 300 g/mol (determined with GPC RI or GPC MALLS).

Alternan-oligosaccharide of the first invention consists of alternan molecules having a degree of polymerization in the range of 3-30, wherein minor amounts of molecules with a DP of higher than 30 might be present. In a another embodiment, alternan-oligosaccharide according to the invention consists of molecules having a degree of polymerization (DP) in the range of 3-26, preferably in the range of 3-20, more preferably in the range of 3-18, still more preferably in the range of 3-15, especially preferably in the range of 3-12, and most preferably in the range of 3-10, wherein minor amounts of molecules with a DP of higher than the given upper limits might be present.

The term "minor amounts" means an amount of less than 5.0 percent by weight based on the total weight of alternan-oligosaccharide, preferably an amount of less than 3.0 percent by weight, more preferably less than 2.0 percent by weight, still more preferably less than 1.0 percent by weight, most preferably less than 0.5 percent by weight.

In the first invention the singular-term "alternan-polysaccharide" designates both monodisperse alternan-polysaccharides with molecules of only one degree of polymerization (DP) as well as polydisperse alternan-polysaccharides with molecules having different degrees of polymerization.

In the first invention the singular-term "alternan-oligosaccharide" designates both monodisperse alternan-oligosaccharides with molecules of only one degree of polymerization (DP) as well as polydisperse alternan-oligosaccharides with molecules having different degrees of polymerization.

Alternan-oligosaccharides are well known from the state of the art and for example disclosed together with manufacturing processes in WO 00/47727, U.S. Pat. No. 7,182,954 WO 2006/088884, and Cote and Robyt 1982, *Carbohydrate Research*, 111:127-142 which are incorporated by reference in their entirety in the present description. Alternan-oligosaccharides can be produced by the reaction of sucrose with an acceptor molecule, or without an acceptor molecule, as explained below.

Alternan-oligosaccharides can be produced from alternan polysaccharides by degradation of alternan polysaccharides under appropriate conditions. The degradation can for example be an enzymatic degradation of alternan polysaccharides or a degradation under acidic conditions, preferably with heating.

Alternan-oligosaccharides can also be produced by the reaction of sucrose with an acceptor molecule in presence of alternansucrase enzyme.

Alternan-oligosaccharides may be prepared by a method, wherein
a) a sucrose containing solution is contacted with a catalytically effective amount of alternansucrase enzyme and acceptor molecules under conditions permitting the conversion of sucrose to alternan-oligosaccharide and fructose; and
b) alternan-oligosaccharide and fructose are isolated from the solution.

The reaction may be conducted between room temperature and 37° C. and at a pH between about 4.7 and 7, and may be allowed to proceed until the sucrose has been essentially consumed. Detailed reaction conditions are disclosed in WO 00/47727, U.S. Pat. No. 7,182,954 and in the appended example. The product is usually obtained as a syrup which may further be purified, i.e. by membrane filtration, and/or dried.

The acceptor molecule is understood to mean a molecule at which an alternansucrase is able to catalyze a chain-extending reaction. The acceptor which can be added to the reaction mixture at the beginning of the reaction is preferably a carbohydrate or a carbohydrate derivative. The use of external acceptors leads to the production of low molecular alternan-oligosaccharides. The carbohydrate acceptor is preferably a saccharide selected from the group consisting of maltose, isomaltose, maltitol, (iso)maltotriose and methyl-α-D-glucan. Other preferred acceptor molecules are glucose, gentiobiose, raffinose, melibiose, isomaltitol, isomaltooligosaccharide, theanderose, kojibiose, glucosyl trehaloses, cellobiose, maltotetraose, nigerose, lactose, panose or mixtures thereof.

Depending upon the particular acceptor selected, the glucosyl units will generally be added through an α(1,6) linkage, or through an α(1,3) linkage if an α(1,6) linkage is already present. Alternan-oligosaccharides are obtained which have a lower molecular weight than the alternan that can be prepared in the absence of external acceptors. The reaction will typically produce a mixture of oligosaccharides having different degrees of polymerization (DP). If alternan-oligosaccharides are produced by the reaction of sucrose with an acceptor molecule, the degree of polymerization (DP) is defined as the number of D-glucosyl units added onto the original acceptor molecule plus the number of monosaccharide units in the original acceptor oligosaccharide.

The extent of the degree of polymerization may vary with the concentrations and the relative ratio of sucrose and acceptor oligosaccharide. The reaction product will generally be composed of a mixture of oligosaccharides having different degrees of polymerization. At a relatively high sucrose:acceptor ratio, more glucosyl units are transferred into glucan and products with higher degree of polymerization are obtained (i.e. the relative amounts of the high DP oligosaccharides in the product will be increased). In contrast, at a low sucrose:acceptor ratio, the predominant reaction product is that resulting from the transfer of a single glucosyl unit to the acceptor. Thus, the yields of oligosaccharides of a desired degree of polymerization may be optimized by varying the sucrose:acceptor ratio. The precise sucrose:acceptor ratios for a desired degree of polymerization will vary with the particular acceptor oligosaccharide and may be readily determined by routine experimentation.

In still another embodiment, alternan-oligosaccharides can be produced by the reaction of sucrose in presence of alternansucrase enzyme, and without using an acceptor molecule.

Alternansucrase for use herein may be obtained from a variety of microorganisms, preferably strains of *Leuconostoc* and particularly strains of *L. mesenteroides*, as for example disclosed in WO 00/47727. In one embodiment, the enzyme is produced by strains of which secrete a high proportion of alternansucrase to dextransucrase such as described by Leathers et al., U.S. Pat. No. 5,702,942, the contents of which are incorporated by reference herein. In another embodiment the alternansucrase enzymes that can be used to produce alternan-oligosaccharides include *Leuconostoc mesenteroides* strains NRRL B 1355, 23185, 23186, 23188, 23311, 21297, 30821, 30894 These enzymes can be additionally cloned and expressed recombinantly, such as described in Gilles Joucla, Doctoral Dissertation, Ingenier INSA, Toulouse, France, 2003.

Production of the alternansucrase may be conducted by culture of any of the above-mentioned microorganisms using conventional techniques and under aerobic conditions which are effective to promote growth and production of the enzyme such as described in Leathers et al. or the example herein below. Following culture, the enzyme may be isolated or separated from the microorganisms using conventional techniques, such as by centrifugation or filtration.

The term "degradation-resistant" in the first invention means that the degree of polymerization of alternan does not measurably (High performance anion-exchange chromatography—HPAEC or Gel permeation chromatography—GPC-RI) decrease in acidic environment of pH 3, over a time period of at least 3 weeks when the sample is stored at room temperature (20° C.).

However, alternan oligosaccharide turned out to be even more stable. The degree of polymerization of alternan oligosaccharide does not measurably (High performance anion-exchange chromatography—HPAEC or Gel permeation chromatography—GPC-RI) decrease in acidic environment of pH 6 or below, preferably pH 3 or below, over a time period of at least 8 weeks when the sample is stored at a temperature of up to 32° C.

A main product of degradation of alternan is glucose and the degradation mechanism normally takes place by hydrolysis of alternan chains. Because of its degradation-resistance, alternan is excellently suitable as a degradation-resistant prebiotic and/or low glycemic and/or soluble fiber ingredient for acidic foodstuffs. Moreover, all other beneficial properties of alternan that have been described in the prior art are retained due its degradation resistance.

The term "foodstuff" as used herein also encompasses beverages and the term "acidic foodstuff" also encompasses "acidic beverages". The acidic foodstuff is defined as a foodstuff having a pH below 7. The acidic foodstuff has in one embodiment a pH of 6 or below, more preferably a pH of 3.5 or below, still more preferably a pH of <3 (below 3). In still another embodiments the acidic foodstuff has a pH in the range of 1 to 6, more preferably 1 to 5, still more preferably 1 to 4 and most preferably 1.5 to 3.5. Another advantageous pH ranges are pH 3 to 6 and pH 1 to <3.

In a special embodiment, the acidic foodstuff is an acidic beverage and alternan-oligosaccharide is used as ingredient in the beverage. The acidic beverage has preferably a pH of 6 or below, more preferably a pH of 3.5 or below, still more preferably a pH of <3 (below 3). In still another embodiments the acidic beverage has a pH in the range of 1 to 6, more preferably 1 to 5, still more preferably 1 to 4 and most preferably 1.5 to 3.5. Another advantageous pH range is pH 3 to 6 and pH 1 to <3.

Another beneficial property of alternan is degradation-resistance in acidic environment even at elevated temperatures.

In the first invention it is shown that alternan polysaccharide is degraded to a minor amount in aqueous environment of pH 3-4 when heated to a temperature of up to 60° C. for 1 hour. Alternan polysaccharide is deemed to have acceptable stability with minor degradation even at 70° C. under these conditions. Thus, alternan-polymer is a suitable as a degradation-resistant ingredient for acidic foodstuffs with pH 3 as a lower pH limit, which are subjected to a heating step at a temperature of up to 60-70° C. Degradation is detected by increase of glucose (High performance anion-exchange chromatography—HPAEC or Gel permeation chromatography—GPC-RI) in a heated sample as degradation product of alternan-polymer.

Alternan-oligosaccharide turned out to be even more stable. In the first invention it is shown that alternan-oligosaccharide is not measurably degraded in aqueous environment of pH 3 or above when heated to a temperature of up to 120° C. for 1 hour. In aqueous environment of pH 1.5 alternan-oligosaccharide is not measurably degraded when heated to a temperature of up to 95° C. for 1 hour. No measurable degradation in this context means that no increase of glucose is detected (High performance anion-exchange chromatography—HPAEC or Gel permeation chromatography—GPC-RI) in a heated sample as degradation product of alternan-oligomers.

This property of alternan-oligosaccharide is particularly and without limitation beneficial in the manufacturing process of an acidic beverage since the beverages are sometimes heated to higher temperatures during the process. Some beverage processes call for hot filling. This involves for example heating the beverage to 80-90° C., holding for about 10 minutes at that temperature, cooling to about 65° C. and then bottling. The alternan-oligosaccharide can withstand this heat abuse for at least about 10 minutes without visible effects.

Based on the above finding, the first invention is also directed to the use of alternan (alternan-oligosaccharide or alternan-polysaccharide) as ingredient for acidic foodstuffs, wherein the foodstuff is subjected to a heating step during its manufacture.

In one embodiment of the first invention the foodstuff is subjected to a heating step at a temperature of at least 60° C.

In another embodiment, the first invention is directed to the use of alternan-oligosaccharide as ingredient for acidic foodstuffs, wherein the foodstuff is subjected to a heating step at a temperature of 60-150° C., more preferably 75-150° C., still more preferably 80-130° C., most preferably 80-120° C. In still another embodiment, the heating step is carried out at 60-120° C.

Exemplary time periods of heating may be 5-3600 seconds or 5-1800 seconds, particularly 5-300 seconds, more preferably 5-200 seconds, even more preferably 5-100 seconds, especially preferably 5-60 seconds and most preferably 10-30 seconds. Each of these time periods can be combined with each of the temperatures specified above.

A well known heating method is pasteurization which is commonly used in the manufacture of dairy products, milk, ice creams, beverages, beer, canned foods, sauces, and soups. A pasteurization step is usually conducted at a temperature of about 60° C. to about 100° C., preferably at about 75° C. to about 85° C., for a time of about 10 seconds to about 30 minutes, preferably for at least about 25 seconds. Pasteurization may be conducted by either high temperature short time (HTST) or low temperature long time (LTLT) processing.

Other common heating methods are sterilization and ultra high temperature (UHT) processing. In the first invention said methods are performed as commonly known to an expert skilled in the art. A UHT treatment is commonly undertaken at a temperature of 90-150° C., more preferably 95-150° C., even more preferably 100-150° C., and most preferably at 110° C.-150° C. and a UHT treatment period is commonly 5-300 seconds, more preferably 5-200 seconds, even more preferably 5-100 seconds, especially preferably 5-60 seconds and most preferably 10-30 seconds.

The invention is further directed to acidic foodstuffs comprising alternan as ingredient. Alternan may be used as a degradation-resistant prebiotic and/or low glycemic and/or soluble fiber ingredient. Preferred acidic foodstuffs are selected from beverages, fruits, vegetables, canned foodstuffs, especially canned fruits, canned fish, canned vegetables, bakery products, cake, ready to serve meals, dairy products, as yogurt and buttermilk, and acidic beverages.

The acidic foodstuff of the first invention may have a pH as already defined above. Moreover, the acidic foodstuff of the first invention may be a foodstuff which is subjected to a heating step during its manufacture.

In one embodiment of the first invention the acidic foodstuff is subjected to a heating step at a temperature of at least 60° C. In other embodiments of the first invention the acidic foodstuff is subjected to a heating step of 60-150° C., more preferably 75-150° C., still more preferably 80 to 130° C., most preferably 80-120° C. In still another embodiment, the heating step is carried out at 60-120° C. Heating methods and heating times were already described above.

Alternan may be added to the foodstuff according to the invention in an amount of 0.1 to 20 weight % based on the total weight of the foodstuff more preferably in an amount of 0.1 to 10 weight-%, still more preferably in an amount of 0.1 to 5 weight-%.

The acidic foodstuff is in one embodiment an acidic beverage with a pH in the range as defined above, which contains alternan-oligosaccharide as ingredient. The beverage is preferably selected from fruit juices, energy drinks, lemonades, sherbets, sodas, soft drinks, and flavored waters.

The beverage according to the invention may be a clear beverage. Besides its degradation resistance, a further beneficial property of alternan-oligosaccharide is its ability to retain the clarity of a clear beverage when it is added to a clear beverage formulation as a prebiotic and/or low glycemic and/or soluble fiber ingredient. Clarity can be determined using the test procedure described in WO2006/088884 or evaluated visually on a qualitative basis, as shown in the appended examples.

In another aspect, the invention provides with methods for manufacturing an acidic beverage as described above. In one method for manufacturing a beverage, alternan-oligosaccharide is blended with other ingredients to form a premix which is subsequently added to the water basis of the beverage. Alternan-oligosaccharide can be blended with one or more further ingredients such as vitamins, minerals, sugar alcohols, high intensity sweeteners, flavors, flavor enhancers, acids, as citric acid or malic acid, and conventional sweeteners. In another embodiment only alternan-oligosaccharide added to the ready made beverage. In principle, all manufacturing methods for beverages which are known to an expert skilled in the art can be employed without limitation.

The acidic foodstuff of the first invention does in one embodiment not comprise foodstuffs, syrups or alternan-oligosaccharides (also named. as oligoalternans) as disclosed in the publication WO 2006/088884 and the use of alternan as ingredient for acidic foodstuffs does in one embodiment not comprise the use of a syrup or of alternan-oligosaccharides (also named as oligoalternan) as disclosed in the publication WO 2006/088884.

The second invention relates to the use of alternan as a heat stable ingredient in a foodstuff, a method for manufacturing a foodstuff, comprising the addition of alternan as an ingredient to the foodstuff formulation and a heating step, and to a foodstuff comprising alternan as ingredient, wherein the foodstuff was subjected to a heating step during its manufacture.

Many nutritional ingredients, as dietary fibers, are heat sensitive. Dietary fiber is an important component of the diet but many consumers find dietary fibers unpalatable. Some dietary fibers, as resistant starches (RS), which many consumers find more palatable, do not retain their high dietary fiber content under harsh processing conditions, resulting in products with less dietary fiber than theoretically anticipated. Many foods are subjected to harsh processing conditions, such as homogenization of high moisture food formulations including puddings and yogurts and further pasteurization at temperature 70° C. or higher, retorting where temperature is at 121° C. for prolonged period of time, and/or extrusion of low moisture food products including snacks and breakfast cereals. As harsh processing is used to produce a number of common food compositions, this has been seen as a major impediment to the adoption and use of dietary fibers in such processed food compositions.

US20070275123A1 suggests the use of a modified starch to increase the dietary fiber content of food compositions processed under harsh conditions. By using certain modified starches, food formulations may be harshly processed while retaining substantial dietary fiber. Further, modified starches as described in US20070275123 A1 provide dietary fiber without the negative effects on textural or organoleptic properties of the food compositions which are typically associated with the addition of other dietary fiber sources.

In order to keep the total dietary fiber content high, alternative sources of fiber have been used. However, there is still a demand for heat stable functional ingredients for nutritional purposes.

Surprisingly, it has been found in the second invention that by using alternan as an ingredient, food compositions may be subjected to harsher processing conditions while avoiding a heat-degradation of the ingredient.

The second invention is directed to the use of alternan as a heat stable ingredient in a foodstuff formulation.

The second invention is further directed to the use of alternan as a heat-stable ingredient in a manufacturing method for a foodstuff and to a method for manufacturing a foodstuff, comprising the addition of alternan as an ingredient to a foodstuff formulation and a heating step.

Alternan is deemed to have prebiotic properties (Lopez-Munguia et al Enzyme Microb, Technol. 15 (1993)). Other beneficial properties have been described. According to U.S. Pat. No. 5,702,942 and U.S. Pat. No. 5,789,209 alternans have unique properties that resemble certain functional characteristics of gum arabic, maltodextrins or polydextrose (G. L. Cote, Carbohydrate Polymers 19:249-252 (1992)). Moreover, according to U.S. Pat. No. 5,702,942 and U.S. Pat. No. 5,789,209 alternan has potential commercial applications as a low-viscosity bulking agent and extender in foods and cosmetics, so that alternans have value as noncaloric, carbohydrate-based soluble dietary fiber.

In the second invention it is shown that alternan is stable under high temperature and could therefore retain the above-mentioned properties when used as a heat stable ingredient in a foodstuff formulation or in a manufacturing method for a foodstuff which comprises a heating step, respectively. In similar manner, the low glycemic properties and soluble fiber properties of alternans are retained since no glucose is released from the alternan molecules.

The term "alternan" according to the second invention encompasses alternan-polysaccharide and alternan-oligosaccharide, wherein both types of alteran differ in their molecular weights, as further defined below.

Alternan according to the second invention is a saccharide composed of glucose units. The glucose units are linked to each other via $\alpha$-1,3- and $\alpha$-1,6-glycosidic bonds, and said two types of bonds predominantly appear alternatingly. Alternan may contain branches (Seymour et al., Carbohydrate Research 74, (1979), 41-62).

Alternan-polysaccharide according to the definition of the second invention has a weight average molecular weight Mw of more than 3 000 g/mol, preferably more than 5 000 g/mol (determined with GPC RI or GPC MALLS). In another embodiment, alternan-polysaccharide has a weight average molecular weight Mw in the range of 10 000 000 g/mol to 60 000 000 g/mol (determined with GPC MALLS), more preferably in the range of 12 000 000 g/mol to 50 000 000 g/mol.

In a special embodiment, alternan-polysaccharide is produced with alternansucrase originating from *Leuconostoc Mesenteroides* as described in WO 00/47727 and shows a weight average molecular weight Mw in the range of 33 000 000 g/mol to 60 000 000 g/mol (determined with GPC MALLS), more preferably in the range of 33 000 000 g/mol to 50 000 000 g/mol. In still another special embodiment, alternan-polysaccharide is produced with truncated alternansucrase enzyme as described in PCT/EP2008/051760 and shows a weight average molecular weight Mw in the range of 12 000 000 g/mol to 30 000 000 g/mol (GPC MALLS), more preferably in the range of 14 000 000 g/mol to 28 000 000 g/mol, still more preferably in the range of 16 000 000 g/mol to 26 000 000 g/mol, most preferably 18 000 000 g/mol to 23 000 000 g/mol. Truncated alternansucrase enzymes, methods for producing alternan-polysaccharide therefrom as well as the alternan-polysaccharide itself are described in PCT/EP2008/051760, which is incorporated herein by reference in its entirety.

The weight average molecular weight Mw of alternan-oligosaccharide in the definition of the second invention is 3 000 g/mol or below, preferably 2 500 g/mol or below, more preferably 2 000 g/mol or below, still more preferably 1 500 g/mol or below and most preferably 1 300 g/mol or below (determined with GPC RI or GPC MALLS). Thus the weight average degree of polymerization DPw of alternan oligosaccharide according to the invention is 18.5 or below, preferably 15.4 or below, more preferably 12.3 or below, still more preferably 9.3 or below and most preferably 8.0 or below (DPw=Mw/162 g/mol, 162 g/mol=molecular weight of monomeric glucose unit). The lower limit of the weight average molecular weight Mw of alternan-oligosaccharide is in another embodiment 800 g/mol (DPw=4.9) and the Mw of alternan-oligosaccharide is in the range of 800 g/mol to 3 000 g/mol, preferably 800 g/mol to 2 500 g/mol, more preferably 800 g/mol to 2 000 g/mol, still more preferably 800 g/mol to 1 500 g/mol and most preferably 800 g/mol to 1 300 g/mol (determined with GPC RI or GPC MALLS).

Alternan-oligosaccharide of the second invention predominantly consists of alternan molecules having a degree of polymerization in the range of 3-30, wherein minor amounts of molecules with a DP of higher than 30 might be present. In a another embodiment, alternan-oligosaccharide according to the invention consists of molecules having a degree of polymerization (DP) in the range of 3-26, preferably in the range of 3-20, more preferably in the range of 3-18, still more preferably in the range of 3-15, especially preferably in the range of 3-12, and most preferably in the range of 3-10, wherein minor amounts of molecules with a DP of higher than the given upper limits might be present.

The term "minor amounts" means an amount of less than 5.0 percent by weight based on the total weight of alternan-oligosaccharide, preferably an amount of less than 3.0 percent by weight, more preferably less than 2.0 percent by weight, still more preferably less than 1.0 percent by weight, most preferably less than 0.5 percent by weight.

In the second invention the singular-term "alternan-polysaccharide" designates both monodisperse alternan-polysaccharides with molecules of only one degree of polymerization (DP) as well as polydisperse alternan-polysaccharides with molecules having different degrees of polymerization.

In the second invention the singular-term "alternan-oligosaccharide" designates both monodisperse alternan-oligosaccharides with molecules of only one degree of polymerization (DP) as well as polydisperse alternan-oligosaccharides with molecules having different degrees of polymerization.

Alternan-oligosaccharides are well known from the state of the art and for example disclosed together with manufacturing processes in WO 00/47727, U.S. Pat. No. 7,182,954 WO 2006/088884, and Cote and Robyt 1982, *Carbohydrate Research*, 111:127-142 which are incorporated by reference in their entirety in the second description. Alternan-oligosaccharides can be produced by the reaction of sucrose with an acceptor molecule, or without an acceptor molecule, as explained below.

Alternan-oligosaccharides can be produced from alternan polysaccharides by degradation of alternan polysaccharides under appropriate conditions. The degradation can for example be an enzymatic degradation of alternan polysaccharides or a degradation under acidic conditions, preferably with heating.

Alternan-oligosaccharides can also be produced by the reaction of sucrose with an acceptor molecule in presence of alternansucrase enzyme.

Alternan-oligosaccharides may be prepared by a method, wherein a) a sucrose containing solution is contacted with a catalytically effective amount of alternansucrase enzyme and acceptor molecules under conditions permitting the conversion of sucrose to alternan-oligosaccharide and fructose; and b) alternan-oligosaccharide and fructose are isolated from the solution.

The reaction may be conducted between room temperature and 37° C. and at a pH between about 4.7 and 7, and may be allowed to proceed until the sucrose has been essentially consumed. Detailed reaction conditions are disclosed in WO 00/47727, U.S. Pat. No. 7,182,954 and in the appended example. The product is usually obtained as a syrup which may further be purified, i.e. by membrane filtration, and/or dried.

The acceptor molecule is understood to mean a molecule at which an alternansucrase is able to catalyze a chain-extending reaction. The acceptor which can be added to the reaction mixture at the beginning of the reaction is preferably a carbohydrate or a carbohydrate derivative. The use of external acceptors leads to the production of low molecular alternan-oligosaccharides. The carbohydrate acceptor is preferably a saccharide selected from the group consisting of maltose, isomaltose, maltitol, (iso)maltotriose and methyl-α-D-glucan. Other preferred acceptor molecules are glucose, gentiobiose, raffinose, melibiose, isomaltitol, isomaltooligosaccharide, theanderose, kojibiose, glucosyl trehaloses, cellobiose, maltotetraose, nigerose, lactose, panose or mixtures thereof.

Depending upon the particular acceptor selected, the glucosyl units will generally be added through an α(1,6) linkage, or through an α(1,3) linkage if an α(1,6) linkage is already present. Alternan-oligosaccharides are obtained which have a lower molecular weight than the alternan that can be prepared in the absence of external acceptors. The reaction will typically produce a mixture of oligosaccharides having different degrees of polymerization (DP). If alternan-oligosaccharides are produced by the reaction of sucrose with an acceptor molecule, the degree of polymerization (DP) is defined as the number of D-glucosyl units added onto the original acceptor molecule plus the number of monosaccharide units in the original acceptor oligosaccharide.

The extent of the degree of polymerization may vary with the concentrations and the relative ratio of sucrose and acceptor oligosaccharide. The reaction product will generally be composed of a mixture of oligosaccharides having different degrees of polymerization. At a relatively high sucrose:acceptor ratio, more glucosyl units are transferred into glucan and products with higher degree of polymerization are obtained (i.e. the relative amounts of the high DP oligosaccharides in the product will be increased). In contrast, at a low sucrose:acceptor ratio, the predominant reaction product is that resulting from the transfer of a single glucosyl unit to the acceptor. Thus, the yields of oligosaccharides of a desired degree of polymerization may be optimized by varying the sucrose:acceptor ratio. The precise sucrose:acceptor ratios for a desired degree of polymerization will vary with the particular acceptor oligosaccharide and may be readily determined by routine experimentation.

In still another embodiment, alternan-oligosaccharides can be produced by the reaction of sucrose in presence of alternansucrase enzyme, and without using an acceptor molecule.

Alternansucrase for use herein may be obtained from a variety of microorganisms, preferably strains of *Leuconostoc* and particularly strains of *L. mesenteroides*, as for example disclosed in WO 00/47727. In one embodiment, the enzyme is produced by strains of which secrete a high proportion of alternansucrase to dextransucrase such as described by Leathers et al., U.S. Pat. No. 5,702,942, the contents of which are incorporated by reference herein. In another embodiment the alternansucrase enzymes that can be used to produce alternan-oligosaccharides include *Leuconostoc mesenteroides* strains NRRL B 1355, 23185, 23186, 23188, 23311, 21297, 30821, 30894 These enzymes can be additionally cloned and expressed recombinantly, such as described in Gilles Joucla, Doctoral Dissertation, Ingenier INSA, Toulouse, France, 2003.

Production of the alternansucrase may be conducted by culture of any of the above-mentioned microorganisms using conventional techniques and under aerobic conditions which are effective to promote growth and production of the enzyme such as described in Leathers et al. or the example herein below. Following culture, the enzyme may be isolated or separated from the microorganisms using conventional techniques, such as by centrifugation or filtration.

The term "heat stable" in the second invention mean that the degree of polymerization of alternan does not measurably (High performance anion-exchange chromatography—HPAEC or Gel permeation chromatography—GPC-RI) decrease when heated to a temperature of up to 120° C. over a time period of 1 hour at pH 7.

A main product of heat-degradation of alternan is glucose and the degradation mechanism normally takes place by hydrolysis of alternan chains. Because of its heat-stability, alternan is excellently suitable as a heat-stable prebiotic and/or low glycemic and/or soluble fiber ingredient for foodstuffs which are heated during their manufacture. Moreover, all other beneficial properties of alternan that have been described in the prior art are retained due its heat-stability.

As stated above, the second invention is directed to the use of alternan as a heat stable ingredient in a foodstuff formulation. The foodstuff formulation can be subjected to a heating step during the manufacturing process of the foodstuff or even later, e.g. when the foodstuff is heated by the consumer before consumption. In the first sense, i.e. heating during the manufacturing process, the invention is also directed to a method for manufacturing a foodstuff, comprising the addition of alternan as an ingredient to a foodstuff formulation and a heating step. The manufacturing method is not further limited. According to the second invention, alternan can be used in any manufacturing method for foodstuffs which comprises a heating step.

In case of heating during manufacturing process of a foodstuff, the heating step, or at least one of several heating steps, is performed after addition of alternan to the foodstuff formulation. Otherwise alternan would not fulfill the function of a heat-stable ingredient in the sense of the second invention.

The heating step, in the manufacturing method or even later, may be carried out at a temperature of 50 to 150° C., more preferably 60 to 150° C. or 75 to 0.150° C., still more preferably 80-130° C., most preferably 80-120° C. In another embodiment, the heating step is carried out at 60-120° C.

Exemplary time periods of may be 5-3600 seconds or 5-1800 seconds, particularly 5-300 seconds, more preferably 5-200 seconds, even more preferably 5-100 seconds, especially preferably 5-60 seconds and most preferably 10-30 seconds. Each of these time periods can be combined with each of the temperatures specified above.

A well known heating method is pasteurization which is commonly used in the manufacture of dairy products, milk, ice creams, beverages, beer, canned foods, sauces, and soups. A pasteurization step is usually conducted at a temperature of about 60° C. to about 100° C., preferably at about 75° C. to about 85° C., for a time of about 10 seconds to about 30 minutes, preferably for at least about 25 seconds. Pasteurization may be conducted by either high temperature short time (HTST) or low temperature long time (LTLT) processing.

Other common heating methods are sterilization and ultra high temperature (UHT) processing. In the second invention said methods are performed as commonly known to an expert skilled in the art. A UHT treatment is commonly undertaken at a temperature of 90-150° C., more preferably 95-150° C., even more preferably 100-150° C., and most preferably at 110° C.-150° C. and a UHT treatment period is commonly 5-300 seconds, more preferably 5-200 seconds, even more preferably 5-100 seconds, especially preferably 5-60 seconds and most preferably 10-30 seconds.

In another aspect, the second invention is directed to a foodstuff which was subjected to a heating step during its manufacture and which comprises alternan as ingredient. The heating methods as explained above can be applied. The term "foodstuff" as used herein also encompasses beverages.

The foodstuff may be selected from dairy products, ice creams, yogurts, milk, puddings, beverages, beer, sauces, soups, retorted foodstuffs, condiments, canned foodstuffs, especially canned fruits, canned fish, canned vegetables, bakery products, cookies, cake, biscuits, meat products, extrusion products, as snacks and cereals, pasta and ready to serve meals.

Alternan may be added to the foodstuff according to the invention in an amount of 0.1-20 weight-% based on the total weight of the foodstuff, more preferably in an amount of 0.1-10 weight-%, still more preferably in an amount of 0.1-5 weight-%.

In a very special embodiment of the second invention, the foodstuff is an acidic foodstuff, which was subjected to a heating step during its manufacture and which comprises alternan as ingredient. Many foodstuffs which are subjected to a heating step during manufacture have a low pH which further promotes the degradation of valuable ingredients. This is especially true for acidic beverages since beverages are often heated to higher temperatures during the process, e.g. during a hot filling process. Other acidic foodstuffs, as for example dairy products, are commonly subjected to a pasteurization step.

An acidic foodstuff is defined herein as a foodstuff having a pH below 7. The acidic foodstuff may have a pH of 6 or below, more preferably a pH of 3.5 or below, still more preferably a pH of <3 (below 3). In still other embodiments the acidic foodstuff has a pH in the range of 1 to 6, more preferably 1 to 5, still more preferably 1 to 4 and most preferably 1.5 to 3.5. Another advantageous pH ranges are pH 3 to 6 and pH 1 to <3.

Acidic foodstuffs may be selected from canned foodstuffs, especially canned fruits, canned fish, canned vegetables, bakery products, cake, ready to serve meals, dairy products, as yogurt and buttermilk, and acidic beverages.

In a special embodiment, the acidic foodstuff is an acidic beverage. The acidic beverage may have a pH of 6 or below, more preferably a pH of 3.5 or below, still more preferably a pH of <3 (below 3). In still other embodiments the acidic beverage has a pH in the range of 1 to 6, more preferably 1 to 5, still more preferably 1 to 4 and most preferably 1.5 to 3.5. Another advantageous pH ranges are pH 3 to 6 and pH 1 to <3.

The acidic beverage may be selected from fruit juices, energy drinks, lemonades, sherbets, sodas, soft drinks, and flavored waters.

In the second invention it is shown that alternan polysaccharide is only degraded to a minor amount in aqueous environment of pH 3-4 when heated to a temperature of up to 60° C. for 1 hour. Alternan polysaccharide is deemed to have acceptable stability with minor degradation even at 70° C. under these conditions. Thus, alternan-polymer is a suitable as a heat-stable ingredient for acidic foodstuffs with pH 3 as a lower pH limit, which are subjected to a heating step at a temperature of up to 60-70° C. Degradation is detected by increase of glucose (High performance anion-exchange chromatography—HPAEC or Gel permeation chromatography—GPC-RI) in a heated sample as degradation product of alternan-polymer.

In foodstuffs which are still more acidic, as for example some acidic beverages, the preferred ingredient is alternan-oligosaccharide. In the second invention it is shown that alternan-oligosaccharide is not measurably degraded in aqueous environment of pH 3 or above when heated to a temperature of up to 120° C. for 1 hour. In aqueous environment of pH 1.5 alternan-oligosaccharide is not measurably degraded when heated to a temperature of up to 95° C. for 1 hour. No measurable degradation in this context means that no increase of glucose is detected (High performance anion-exchange chromatography—HPAEC or Gel permeation chromatography—GPC-RI) in a heated sample as degradation product of alternan-oligomers.

This property of alternan-oligosaccharide is particularly and without limitation beneficial in the manufacturing process of a beverage since beverages are sometimes heated to higher temperatures during the process. Some beverage processes call for hot filling. This involves for example heating the beverage to 80-90° C., holding for about 10 minutes at that temperature, cooling to about 65° C. and then bottling. The alternan-oligosaccharide can withstand this heat abuse for at least about 10 minutes without visible effects.

The beverage according to the invention may be a clear beverage. Besides its heat-stability, a further beneficial property of alternan-oligosaccharide is its ability to retain the clarity of a clear beverage when it is added to a clear beverage formulation as a prebiotic and/or low glycemic and/or soluble fiber ingredient. Clarity can be determined using the test procedure described in WO2006/088884 or evaluated visually on a qualitative basis.

The foodstuff of the second invention does in one embodiment not comprise foodstuffs, syrups or alternan-oligosaccharides (also named as oligoalternans) as disclosed in the publication WO 2006/088884 and the use of alternan as a heat stable ingredient in a foodstuff does in one embodiment not comprise the use of a syrup or of alternan-oligosaccharides (also named as oligoalternan) as disclosed in the publication WO 2006/088884.

The second invention discloses following subject matter:
1. Use of alternan as a heat stable ingredient in a foodstuff.
2. Use of alternan according to subject matter 1, wherein the foodstuff is subjected to a heating-step at a temperature of 50-150° C.
3. Use according to subject matter 1 or 2 wherein the alternan is an alternan-polysaccharide.
4. Use according to subject matter 1 or 2 wherein the alternan is an alternan-oligosaccharide.
5. Use according to subject matter 4 wherein the alternan-oligosaccharide is produced by the reaction of sucrose with an acceptor molecule in presence of alternansucrase enzyme.
6. Use according to subject matter 5 wherein the acceptor molecule is selected from maltose, isomaltose, maltitol, (iso)maltotriose and methyl-α-D-glucan.
7. Use according to one of the preceding subject matters, wherein the foodstuff is selected from dairy products, ice creams, yogurts, milk, puddings, beverages, beer, sauces, soups, retorted foodstuffs, condiments, canned foodstuffs, especially canned fruits, canned fish, canned vegetables, bakery products, cookies, cake, biscuits, meat products, extrusion products, as snacks and cereals, pasta and ready to serve meals.
8. Use according to one of the preceding subject matters, wherein the foodstuff is an acidic foodstuff.
9. Use according to one of subject matter 4-6, wherein the foodstuff is an acidic beverage with a pH of 6 or below.
10. Method for manufacturing a foodstuff, comprising the addition of alternan as an ingredient to a foodstuff formulation and a heating step.
11. Method according to subject matter 10, wherein the heating step is carried out at a temperature of 50-150° C.
12. Method according to subject matter 10 or 11 wherein the alternan is an alternan-polysaccharide.
13. Method according to subject matter 10 or 11 wherein the alternan is an alternan-oligosaccharide.
14. Method according to subject matter 13 wherein the alternan-oligosaccharide is produced by the reaction of sucrose with an acceptor molecule in presence of alternansucrase enzyme.
15. Method according to subject matter 14 wherein the acceptor molecule is selected from maltose, isomaltose, maltitol, (iso)maltotriose and methyl-α-D-glucan.
16. Method according to one of subject matters 10-15, wherein the foodstuff is selected from dairy products, ice creams, yogurts, milk, puddings, beverages, beer, sauces, soups, retorted foodstuffs, condiments, canned foodstuffs, especially canned fruits, canned fish, canned vegetables, bakery products, cookies, cake, biscuits, meat products, extrusion products, as snacks and cereals, pasta and ready to serve meals.
17. Method according to one of subject matters 10-16, wherein the foodstuff is an acidic foodstuff.
18. Method according to one of subject matters 13-15, wherein the foodstuff is an acidic beverage with a pH of 6 or below.
19. Foodstuff comprising alternan as ingredient, wherein the foodstuff was subjected to a heating step during its manufacture.
20. Foodstuff according to subject matter 19, which is selected from dairy products, ice creams, yogurts, milk, puddings, beverages, beer, sauces, soups, retorted foodstuffs, condiments, canned foodstuffs, especially canned fruits, canned fish, canned vegetables, bakery products, cookies, cake, biscuits, meat products, extrusion products, as snacks and cereals, pasta and ready to serve meals.

21. Foodstuff according to subject matter 19 or 20, which is an acidic foodstuff.

The following examples are intended to further illustrate the inventions and not intended to limit the scope of the inventions which is defined by the claims.

EXAMPLES

Literature

Arguello-Morales M A, Remaud-Simeon M, Pizzut S, Sarcabal P, Willemot R and Monsan P (2000) Sequence analysis of the gene encoding alternansucrase, a sucrose glucosyltransferase from *Leuconostoc mesenteroides* NRRL B-1355. FEMS Microbiol Lett 182: 81-85.

Degenkolb J, Takahashi M, Ellestad G A, Hillen W, 1991: Antimicrob. Agents Chemother. 35, No 8, 1591-1595 Structural requirements of tetracycline-Tet repressor interaction: Determination of equilibrium binding constants for tetracycline analogues with the Tet repressor.

Dotto G P, Horiuchi K, Zinder N D (1982) Initiation and termination of phage f1 plus-strand synthesis. Proc Natl Acad Sci USA. 79:7122-7126.

Horn, U., Strittmatter, W., Krebber, A., Knüpfer, U., Kujau, M., Wenderoth, R., Müller, K., Matzku, S., Pliickthun, A., and Riesenberg, D. (1996) High volumetric yields of functional dimeric miniantibodies in *Escherichia coli*, using an optimized expression vector and high-cell-density fermentation under non-limited growth conditins. Appl. Microbio. Biotechnol. 46, 524-532.

Jeong S H, Bae I K, Lee J H, Sohn S G, Kang G H, Jeon G J, Kim Y H, Jeong B C and Lee S H. (2004) Molecular Characterization of Extended-Spectrum Beta-Lactamases Produced by Clinical Isolates of *Klebsiella pneumoniae* and *Escherichia coli* from a Korean Nationwide Survey. J Clin Microbiol 42: 2902-2906.

López-Muguia, A., Pelenc, V., Remaud, M., Biton, J. I, Michel, J. M., Lang, C., Paul, F., Monsan, P. (1993). Production and purification of alternansucrase, a glucosyltransferase from *Leuconostoc mesenteroides* NRRL B-1355, for the synthesis of oligoalternan: Enzyme Microb. Technol., 15, 77-85.

Schmidt T G M and Skerra A (1993). The random peptide library-assisted engineering of a C-terminal affinity peptide, useful for the detection and purification of a functional Ig Fv fragment. Protein Eng 6: 109-122.

Skerra, A (1994). Use of the tetracycline promoter for the tightly regulated production of a murine antibody fragment in *Escherichia coli*. Gene 151, 131-135.

1. Fermentative Production of Alternansucrase from *Leuconostoc mesenteroides*

For heterologous expression of the alternansucrase (ARS) from *Leuconostoc mesenteroides* strain NRRL B-1355, the gene encoding alternansucrase has been isolated, fused to a Strep-tag (IBA BioTAGnology, Gottingen, Germany) and cloned into vector pAI-B-AlSu under the control of a tetraycline-inducible promoter.

The genetically modified *E. coli* strain DH5a pAIB-AlSu Q29 employed for fermentation harbours plasmid pAI-B-AlSu for cytoplasmic expression of alternansucrase from *Leuconostoc mesenteroides*. Vector pAI-B-AlSu is essentially derived from plasmid pASK-IBA-3 (purchased from IBA Gottingen; www.iba-go.com). It contains the coding sequence of alternansucrase derived from *Leuconostoc mesenteroides* strain NRRL B-1355 fused to a 8 aminoacid peptide strep-tag at the C-terminal end. The strep-tag is linked to the protein through a 2 aminoacid linker. Expression of alternansucrase is under the transcriptional control of the tetA promoter/operator and repressor. The tetA promoter is tightly regulated by the tet repressor which is encoded on the same plasmid and is constitutively expressed from the β-lactamase promoter. In this way, expression of alternansucrase is stringently repressed until efficient chemical induction by tetracycline or anhydrotetracycline, AHT, (Degenkolb et al.; 1991).

Vector Pai-B-AlSu Contains the Following Genetic Elements:

| Nt Positions | Orientation | Origin |
|---|---|---|
| 37-72 | Clockwise | PTet: Tet Promoter from transposon Tn10 (Skerra, 1994) |
| 139-6309 | Clockwise | asrLm: Coding sequence of the Alternansucrase gene from *Leuconostoc mesenteroides* NRRL B-1355. (Arguello-Morales et al., 2000) |
| 6310-6315 | Clockwise | SA linker encoding 2 Amino Acids: Serine and Alanine |
| 6316-6345 | Clockwise | StrepTag: sequence encoding a 8 AA peptide selected from a genetic fusion peptide library for its ability to bind to streptavidin (Schmidt and Skerra, 1993) |
| 6439-6877 | Clockwise | f1 origin: origin of replication from filamentous phage f1 (Dotto et al., 1982) |
| 7026-7886 | Clockwise | AmpR: Coding sequence of β-lactamase from *Escherichia coli*, conferring Ampicillin resistance (Jeong et al., 2004) |
| 7896-8519 | Clockwise | TetR: Tet repressor domain from Transposon Tn10 (Skerra, 1994) |

For fermentation, vector pAI-B-AlSu is transformed in *E. coli* K12 DH5α and bacterial cells harbouring the vector are selectively grown for 12 h at 37° C. to an OD600 of 65 in mineral medium (Horn et al., 1996) supplemented with ampicillin (100 μg/ml). Expression of the alternansucrase is induced by the addition of anhydrotetracyclin (0.2 mg/l) and further cultivation for 5 h at 25° C. to an OD600 of 140. For purification of the enzyme, the bacterial cells are harvested by centrifugation (20000 rpm; 20 min) and solubilized in resuspension buffer (100 mM NaAc, pH 5.3).

The cells are disrupted using a high pressure homogenizer (two cycles, 1200 bar). Bacterial nucleic acid is degraded by DNase/RNase (3 mg/l) treatment and the resulting extract is centrifuged (3,800 g for 15 min at 4° C.) to harvest the insoluble cell matter including the bacterial inclusion bodies.

The supernatant is discarded and the pellet is resuspended 8 M urea, 50 mM NaAc buffer, pH 5.3 and kept on ice while shaking for one hour. Subsequently, the remaining debris is removed by centrifugation at 10.000 g for 15 min. Renaturation is then performed by 20-fold dilution in 0.5 M urea, 2.5 mM CaCl2, 100 mM NaAc, pH 5.3. Aliquots of the mixture are immediately frozen in liquid nitrogen and stored at −20° C.

Activity of alternansucrase can be determined as described by Lopez-Munguia et al., 1993.

2. Production of Alternan-Oligosaccharides with Acceptor Molecule Maltose (Maltose Oligosaccharides)

For the production of maltose oligosaccharides, the purified alternansucrase enzyme as described in 1 is incubated with 10% sucrose (w/v) and 4.5-5% maltose (w/v) in a 50 mM sodium acetate buffer pH 5.3 at room temperature for approximately 72 hours. For the incubation, 50 units of alternansucrase per liter reaction mix are used. Alternan, which accumulates as a by-product, is precipitated by adding analytical grade ethanol to a final concentration of 50% (v/v). The mixture is centrifuged at 4000 rpm for 10 min and the resulting precipitate is discarded.

Maltose oligosaccharide is prepared by further concentrating the obtained precipitate using a vacuum vaporizer (Buechi Rotavapor R-220) to about 70° brix. Maltose oligosaccharide is obtained as a syrup which is further purified and dried to obtain the final product.

3. Production of Alternan-Polysaccharide

Plasmid pAI-B-AlSu Q29 (cf. Example 1 above) was transformed in *E. coli* DH5a. The cells were pre-cultured in mineralmedium (Horn et al., 1996) with 100 µg/ml Ampicillin and 10% LB medium. Mineralmedium, without LB, was inoculated with this pre-culture. The cells were grown at 37° C., induced with Anhydrotetracyclin (AHT) (0.2 mg/L), and grown further at 25° C. The cells were harvested, resuspended in [10 mM MOPS pH 7.6; 2.5 mM CaCl2 and 0.05% Triton X-100] and extracted with a high pressure homogenisator. The cell lysate was centrifuged at 20 000 rpm for 20 minutes at 4° C. The supernatant was filtered over a 0.22 µm filter.

Alternan was produced in a 60 L Biotransformation containing 0.13% Acetic Acid, 100 mM NaAc pH5.3, 20% Sucrose, 1 mM DTT, 1600 ml filtered protein extract (ca. 3900 Units). The reaction mixture was incubated for 60 h. at 37° C. The polymer was precipitated with 60 L Technical Ethanol 40 h 4° C., washed 2× with 60 L 60% Technical Ethanol, and 1× with 60 L 60% Ethanol Absolute. The product was dried through lyophilization.

4. Application Testing in Flavored Waters

Two retail flavored waters were testes in an application study. Alternan-oligosaccharide (also designated hereinafter as "maltose oligosaccharide" because auf maltose acceptor) produced as described in Example 2 was used for the tests.

| Beverage Name | pH | Comments |
| --- | --- | --- |
| Metro Mint ® (Soma Beverage Co.) | 5.87 | Clear, colorless |
| Fruit2O ® (Kraft) | 3.02 | Clear, colorless |

Set Up
   Storage Temperatures: −17.8° C., 4.4° C., 21° C., 32.2° C.
   Evaluation Points: 0 Time, 1 Week, 4 Weeks, 8 Weeks
Beverage Production
   Alternan-oligosaccharide was combined with the flavored waters in a large batch.
   Alternan-oligosaccharide was added to the water while agitating with a Lightning Mixer at 700 rpm. After the entire amount of alternan-oligosaccharide was added, the beverage was mixed for an additional 1.5 minutes.
   The percentages used in the preliminary screening were used for the shelf life. Each variable is present at a level to give a 5 gram per serving level of fiber.
   After mixing, the beverage was aliquoted to separate bottles for storage. The bottles were placed in storage at each temperature.
   One bottle was used for each evaluation point.
   The samples were allowed to come to room temperature before evaluation.
   The following protocols were used to evaluate the beverages at each interval in the shelf life study.
4.1 Specific Gravity—BRIX
   Bausch & Lomb Abbe-3L Refractometer
   Samples were always at room temperature so temperature control was not used.

The brix of the beverages containing maltose-oligosaccharide did not change during the shelf life period of 8 weeks at different storage temperatures (−17.8° C., 4.4° C., 21° C., 32.2° C.). Even when precipitation was noted, the brix was not significantly affected. Beverages were always shaken before measurement.

4.2 Color
   200 ml sample size in 250 ml Pyrex beaker.
   White filter paper was placed over the top of the beaker
   Readings were taken through the bottom of the beaker making sure that the glass was clean.
   Color was evaluated visually and comments made.

The maltose-oligosaccharide did not develop significant color over the shelf life. The maltose-oligosaccharide sample in 32.2° C. storage did show a very light yellow color at 8 weeks in the acidic beverage.

4.3 Turbidity and Formation of Precipitate
   Turbidity and precipitation was evaluated visually in the samples over the shelf life, with samples stored at different temperatures.

Maltose-oligosaccharide did cause a slight cloudiness in both water systems. The turbidity did not appear to be significantly affected by time and or temperature.

|  | Average Cloudiness Score | Comments |
| --- | --- | --- |
| maltoseoligosaccharide | 0.5 to 1.0 | very slight. |

Scale: 0 = clear,
1 = slight,
2 = slight +,
3 = moderate,
4 = moderate +
7 = very heavy The maltose-oligosaccharide did not form a precipitate under any of the storage conditions.

4.4 Hot Fill Simulation—Abuse Condition

Some beverage processes call for hot filling. This involves heating the beverage to 82° C., holding for 10 minutes at that temperature, cooling to 65° C. and then bottling. The maltose-oligosaccharide beverages were exposed to this heat abuse.

Process
   500 ml of a 2.60% solution of maltose-oligosaccharide in Metro Mint or Fruit₂O water was placed in the top of a double boiler.
   Heated to between 82° C. and 87.8° C.
   Held for 10 minutes at that temperature
   Cooled liquid to 65.6° C.
   Bottled
   Beverages observed for 72 hours. Measured for viscosity, pH, and Brix.
Results:

|  | Viscosity (cp) | pH | Brix | Comments |
| --- | --- | --- | --- | --- |
| Fruit₂O Control | 2.16 | 2.89 | 2.8 |  |
| Fruit₂O Hot fill | 2.16 | 2.94 | 3.0 | No obvious change in appearance. |
| Metro Mint Control | 2.13 | 3.95 | 2.9 |  |
| Metro Mint Hot Fill | 2.19 | 4.17 | 2.9 | No obvious change in appearance. |

The maltose-oligosaccharide was tolerant to the hot fill conditions tested.

4.5 Resistance to Degradation

For the measurements all samples were diluted (total starting volume 1 ml) and neutralized if necessary (Fruit2O: +100 µl 150 mM NaOH).

High performance anion-exchange chromatography—HPAEC: 1:100; injection volume: 25 µl;

HPAEC-PAD: glucan program 45 min

Gel permeation chromatography—GPC: Metromint: 1:5 with DMSO, Fruit2O samples (after neutralisation) 1:2.5

Results:

In the GPC profile no change was detected over the shelf life of the sample (8 weeks).

HPAEC: no changes were detected in fractions over DP3. In Metromint a slight increase in glucose over shelf life was detected at 32.2° C. In Fruit2O sucrose decreased and glucose and fructose increased during shelf life at 32.2° C.

| Metromint | | | Fruit2O | | |
|---|---|---|---|---|---|
| storage temperature/time | $M_w$ g/mol | DP | storage temperature/time | $M_w$ | DP |
| −17.8° C./0 weeks | 920 | 6 | −17.8° C./0 weeks | 896 | 6 |
| −17.8° C./1 week | 916 | 6 | | | |
| −17.8° C./4 weeks | 910 | 6 | −17.8° C./4 weeks | 895 | 6 |
| | | | −17.8° C./8 weeks | 898 | |
| 32.2° C./0 weeks | 909 | 6 | 32.2° C./0 weeks | 901 | 6 |
| 32.2° C./1 week | 906 | 6 | 32.2° C./1 week | 900 | |
| 32.2° C./4 weeks | 909 | 6 | 32.2° C./4 weeks | 903 | 6 |
| 32.2° C./8 weeks | 910 | 6 | 32.2° C./8 weeks | 938 | 6 |

In DP calculations 162 g/mol was used as MW of monomer

5. Resistance to Degradation in Carbonated Beverages

Three retail beverages (Coca Cola®, Fanta® and Orange lemonade) were prepared with alternanoligosaccharide (also designated as maltose-oligosaccharide because of maltose acceptor molecule) and competitive products for the shelf life screening.

Maltose-oligosaccharide was produced according to a procedure similar to Ex. 2, except that 30% sucrose and 15% maltose were used and the ethanol precipitation step was omitted. The product was purified by filtration techniques and maltose-oligosaccharide was obtained as a syrup containing about 15 weight-% fructose.

Set Up

Storage Temperatures: 4° C., RT (24° C.), 37° C.

Evaluation Points: 0 time, 4 days, 1 week, 2 weeks, 4 weeks, 8 weeks

Beverage Production

Maltose-oligosaccharide was combined with the beverage in 50 g batch.

2.5% of maltose-oligosaccharide was used in the screening. Maltose-oligosaccharide was added to the beverage in a 50 ml Falcon. After the entire amount of fiber 5 g of water was added and the beverage was mixed.

After mixing, the 50 g batch was distributed to small beverage amounts (ca. 3 g) and put in small bottles. Those small bottles were used for the shelf life storage at the different conditions.

One bottle was used for each evaluation point.

After each storage time the samples were visually evaluated and then frozen at −18° C. for GPC-RI and HPAEC-PAD measurement.

GPC-RI and HPAEC-PAD Results:

The beverages have been measured for degradation of maltose-oligosaccharide using GPC-RI and HPAEC-PAD at BBS. In none of the three beverages maltose-oligosaccharide showed any degradation during storage over the investigated time range at the different temperatures. The only alteration was to be seen in sucrose content. This effect was most drastic in beverages with lowest pH at 37° C. (Coca Cola® and Fanta®). Sucrose content of orange lemonade also decreased, but to a lower amount.

5.6. Heat and Acid Stability of Alternan-Oligosaccharide

Material: Maltose-oligosaccharide was produced according to a procedure similar to Ex. 2, except that 30% sucrose and 15% maltose were used and the ethanol precipitation step was omitted. The product was purified by filtration techniques and maltose-oligosaccharide was obtained as a syrup containing about 15 weight-% fructose, 68.8° BRIX (internal reference M2).

The maltose-oligosaccharide product had a degree of polymerization (DP) in the range of DP 3-7.

The maltose-oligosaccharide contained about 15 weight-% of fructose. For preparation of samples all amounts were calculated in such manner that >5% pure maltose-oligosaccharide was contained in the final sample.

Samples:

alternan-oligosaccharide in 0.1M HAc-pH 3
alternan-oligosaccharide in 0.02M HCl-pH 1.5

The samples were incubated for 10 minutes at temperatures of 20, 40, 60, 80, and 95° C., respectively, 1 hour at 120° C., and then cooled down for 10 min. 100 µl volumes were taken from each sample and neutralized:

0.1M HAc: 100 µl+100 µl N-Mix HAc (450 µl 1 M NaOH ad 10 ml)

0.02M HCl: 100 µl+100 µl N-Mix HCl (175 µl 1 M NaOH ad 10 ml)

For HPAEC-analysis 50 µl of a 1:400 dilution of the neutralized sample were injected (SC-HPAEC).

The following table shows the relative peak areas of alternan-oligosaccharides.

The results show that no degradation of oligosaccharides (DP 3-7) is detectable up to a temperature of 120° C. in water and acetic acid (pH 3). In HCl (pH 1.5) no degradation is detectable up to a temperature of 95° C. No increase of glucose was detected (data not shown).

At a temperature of 120° C. in HCl degradation was detected, shown by increase of detected glucose (data not shown) and shown by the decrease of relative peak area of DP4-DP7 (see table).

However, it should be taken into account that the 120° C. sample was heated for one hour due to technical reasons (autoclave), which is much longer than for the other samples (10 min).

| Results pH and temperature-stability of alternan-oligomer | | | | | | | |
|---|---|---|---|---|---|---|---|
| | rel. area (%) | | | | | | |
| Sample Name | Panose | DP4-1 | DP4-2 | DP5 | DP6-1 | DP6-2 | DP7 |
| M2 H2O 20° C. | 0.257 | 0.066 | 0.313 | 0.270 | 0.023 | 0.052 | 0.020 |
| M2 H2O 40° C. | 0.257 | 0.066 | 0.313 | 0.269 | 0.023 | 0.052 | 0.019 |
| M2 H2O 60° C. | 0.257 | 0.067 | 0.313 | 0.269 | 0.023 | 0.052 | 0.019 |
| M2 H2O 80° C. | 0.260 | 0.057 | 0.317 | 0.271 | 0.023 | 0.052 | 0.019 |
| M2 H2O 95° C. | 0.257 | 0.067 | 0.314 | 0.269 | 0.023 | 0.052 | 0.019 |
| M2 H2O 120° C. | 0.255 | 0.075 | 0.311 | 0.267 | 0.022 | 0.051 | 0.019 |
| M2 HAc 20° C. | 0.257 | 0.066 | 0.313 | 0.270 | 0.023 | 0.052 | 0.019 |
| M2 HAc 40° C. | 0.259 | 0.057 | 0.316 | 0.272 | 0.023 | 0.052 | 0.020 |
| M2 HAc 60° C. | 0.257 | 0.066 | 0.314 | 0.269 | 0.023 | 0.052 | 0.019 |
| M2 HAc 80° C. | 0.257 | 0.066 | 0.314 | 0.269 | 0.023 | 0.051 | 0.019 |
| M2 HAc 95° C. | 0.257 | 0.066 | 0.313 | 0.269 | 0.023 | 0.052 | 0.019 |

-continued

Results pH and temperature-stability of alternan-oligomer

| | rel. area (%) | | | | | | |
|---|---|---|---|---|---|---|---|
| Sample Name | Panose | DP4-1 | DP4-2 | DP5 | DP6-1 | DP6-2 | DP7 |
| M2 HAc 120° C. | 0.260 | 0.065 | 0.314 | 0.268 | 0.022 | 0.051 | 0.019 |
| M2 HCl 20° C. | 0.257 | 0.066 | 0.313 | 0.270 | 0.023 | 0.052 | 0.019 |
| M2 HCl 40° C. | 0.256 | 0.066 | 0.314 | 0.269 | 0.023 | 0.052 | 0.019 |
| M2 HCl 60° C. | 0.257 | 0.066 | 0.314 | 0.269 | 0.023 | 0.051 | 0.019 |
| M2 HCl 80° C. | 0.260 | 0.057 | 0.317 | 0.271 | 0.023 | 0.052 | 0.020 |
| M2 HCl 95° C. | 0.260 | 0.066 | 0.312 | 0.268 | 0.023 | 0.052 | 0.019 |
| M2 HCl 120° C. | 0.397 | 0.055 | 0.258 | 0.229 | 0.018 | 0.031 | 0.012 |

7. Heat and Acid Stability of Alteman-Polysaccharide
Method 1:
material: alternan-polymer was prepared in concentrations of 1%, 5%, 10% or 0.12%
environments: water (pH 6-7), acetic acid (pH 3.5-5), orange lemonade (pH 3) or hydrochloric acid (pH 1.3-1.5)
temperatures: room temperature (20° C., RT), 40° C., 60° C., 80° C., 95° C., in autoclave only: 120° C.
incubation times: 0.5 h, 1 h, 4 h, 24 h and 2-3 weeks
Method 2:
material: alternan-polymer was prepared in concentrations of 1.25% and 2.5% in orange juice
environments: orange juice (pH 4)
procedure A: alternan is added to cold orange juice, heating to 62.8-65.6° C., pasteurization for 30 min at 62.8° C.
procedure B: alternan is added to preheated orange juice, (62.8° C.), pasteurization for 30 min at 62.8° C.
storage in refrigerator for 1, 3, 7, 10, 20, 30 and 60 days Analysis for both methods was done with GPC MALLS. Results are presented in the following table.

The results show that alternan-polymer is stable at pH 6-7, even when heated. At pH 3-4 alternan-polymer is stable at room temperature. Slight degradation is detected at pH 3-4 when alternan-polymer is heated at 60° C. Considerable degradation is detected at pH 3-4 when alternan-polymer is heated at 80° C.

tion DPw of 8 or below as determined by GPC RI, wherein the prebiotic properties are pH stable.

2. The method according to claim 1, wherein the alternan-oligosaccharide comprises the reaction product of sucrose with an acceptor molecule in the presence of alternansucrase enzyme.

3. The method according to claim 2, wherein the acceptor molecule is maltose, isomaltose, maltitol, (iso)maltotriose, or methyl-α-D-glucan.

4. The method according to claim 1, wherein the acidic foodstuff is beverages, fruits, vegetables, canned foodstuffs, bakery products, cake, ready to serve meals, or dairy products.

5. The method according to claim 1, wherein the acidic foodstuff is subjected to a heating step at a temperature of at least 60° C.

6. The method according to claim 1, wherein the acidic foodstuff is subjected to a heating step at a temperature of 80-130° C.

7. The method of claim 1, wherein alternan is added in an amount of 0.1-10 weight-% based on the total weight of the acidic foodstuff.

8. The method of claim 1, wherein the acidic foodstuff has a pH below 3.

9. The method of claim 1, wherein the foodstuff is subjected to a heating step at a temperature of 80-90° C. for about 10 minutes.

10. The method of claim 1, wherein the foodstuff is subjected to a heating step at a temperature of 80-120° C. for 5-3600 seconds.

11. An acidic foodstuff with prebiotic properties comprising alternan-oligosaccharide having a weight average degree of polymerization DPw of 8 or below as determined by GPC RI, wherein the prebiotic properties are pH stable.

12. The acidic foodstuff according to claim 11, wherein the alternan-oligosaccharide reaction product of sucrose with an acceptor molecule in the presence of alternansucrase enzyme.

13. The acidic foodstuff according to claim 12, wherein the acceptor molecule is maltose, isomaltose, maltitol, isomaltotriose or methyl-α-D-glucan.

Results pH and temperature-stability of alternan-polymer

| pH | T (° C.) | Conc. (%) | incubation | Mw (×10⁷ g/mol) after incubation | Reduction of molar mass* | degradation %* |
|---|---|---|---|---|---|---|
| 6-7 | RT | 5; 10 | 2 weeks at RT | 4.3 | — | none |
| 3-4 | RT | 5; 10 | 3 weeks at RT | 3.1 | — | none |
| 1-1.5 | RT | 5; 10 | 3 weeks at RT | 2.0 | 45% | strong degradation |
| 6-7 | 95 | 1; 5; 10; 12 | 0.5-1 h | 2.8-3.1 | — | none |
| 3-4 | 20-95 | 5 | 1 h | 1.4-3.3 | 20% to 60% | at 60° C. slight degradation, strong degradation at 80° C. and higher |
| 1-1.5 | 20-95 | 5 | 1 h | 0.06-2.7 | 28% to 98% | at 60° C. strong degradation, very strong degradation at 80° C. and higher |
| 4.0 | 62-65 | 1.25; 2.5 | 30 min, then stored at 4° C. for 1 to 60 days | 3.4-4.0 | — | none |
| 6-7 | 120 | 1; 5; 10 | 20 min | 2.8 | — | none |
| 6-7 | 120 | 1; 5; 10 | 1 h | 3.2 | 14%* | none* |
| 3-4 | 120 | 5; 10 | 1 h | 0.2 | 95% | very strong degradation |
| 1-1.5 | 120 | 5; 10 | 1 h | not evaluable | not evaluable | — |

*error is about 14%, therefore degradation can not be evaluated when molar mass is reduced by less than 15%

The invention claimed is:

1. A method of manufacturing an acidic foodstuff with prebiotic properties comprising adding alternan-oligosaccharide as ingredient to an acidic foodstuff, wherein the alternan-oligosaccharide has a weight average degree of polymeriza- 14. The acidic foodstuff according to claim 11, wherein the acidic foodstuff is beverages, fruits, vegetables, canned foodstuffs, bakery products, cake, ready to serve meals, or dairy products.

15. The acidic foodstuff according to claim 11, wherein the foodstuff is subjected to a heating step at a temperature of at least 60° C.

16. The acidic foodstuff according to claim 11, wherein the foodstuff is subjected to a heating step at a temperature of 80-130° C.

17. The acidic foodstuff according to claim 11, comprising alternan in an amount of 0.1-10 weight-% based on the total weight.

18. The acidic foodstuff according to claim 11, wherein the acidic foodstuff has a pH below 3.

* * * * *